United States Patent

Jansen

[11] Patent Number: 5,848,897
[45] Date of Patent: Dec. 15, 1998

[54] TOOTH PROSTHESIS CONSTRUCTION BETWEEN SOUND OR RESTORED ABUTMENT ELEMENTS

[75] Inventor: Jozef Jansen, Drachten, Netherlands

[73] Assignee: Denta Net Holding b.v., Amsterdam, Netherlands

[21] Appl. No.: 616,164

[22] Filed: Mar. 14, 1996

[51] Int. Cl.[6] .................................................. A61C 13/12
[52] U.S. Cl. ............................................. 433/182; 433/193
[58] Field of Search ................................... 433/181, 180, 433/182, 183, 193, 194, 195

[56] References Cited

U.S. PATENT DOCUMENTS

| 1,671,170 | 5/1928 | Takenaka | 433/182 |
|---|---|---|---|
| 1,749,493 | 3/1930 | Lasky | 433/182 |
| 2,609,605 | 4/1952 | Dylan . | |
| 2,826,814 | 3/1958 | Sappey . | |
| 3,710,446 | 1/1973 | Poveromo | 433/182 |

FOREIGN PATENT DOCUMENTS

| 0642767 | 3/1995 | European Pat. Off. . | |
|---|---|---|---|
| 3208915 | 9/1983 | Germany | 433/181 |
| 352782 | 4/1961 | Switzerland . | |
| 2117642 | 10/1983 | United Kingdom . | |

Primary Examiner—Cary E. O'Connor
Attorney, Agent, or Firm—Young & Thompson

[57] ABSTRACT

A construction for a fixed or a removable tooth replacement between two sound or restored abutment elements includes an individually cast plate made of a metal of choice (1), which is provided with an opening of defined size on the approximal side, at the level of the contact point of the abutment, and which is secured on the respective abutment by means of an etching/adhesive bonding technique. An oval adaptation piece (3), (17) with a wedge-shaped or loop-shaped engagement incision at its top, with a tapering opening at the center, and provided with a thread, is cast welded or cemented onto the plate. A movable pin (8) which is milled from metal is guided through the congruent openings of the oval adaptation piece and the plate is cemented in the small channel prepared in the abutment element (20). The pin is secured from the outside by a fastening screw (12).

18 Claims, 8 Drawing Sheets

TOOTH PROSTHESIS CONSTRUCTION BETWEEN SOUND OR RESTORED ABUTMENT ELEMENTS

BACKGROUND OF THE INVENTION

The invention deals with a construction for a tooth prosthesis to be placed between sound or restored abutment elements, which construction has a pin which is to be placed in a hole drilled in the abutment element, and a cavity provided in the tooth prosthesis or in an adaptation piece for receiving the tooth prosthesis for accommodating the pin.

Such construction is known from EP-B-236 264. Said known construction comprises an adaptation piece having dual pins, which both have to be fitted in a hole in the abutment element. This means that in each abutment element, two holes have to be drilled.

The holes should be in a correct position and distanced from each other, so as to ensure a proper fit of the pins. Such proper mutual position of the pins can only be achieved when the drilling is carried out very accurately. The disadvantages here are that this process can only be carried out by very skilled practicians. Moreover, drilling the accurately positioned holes is rather time consuming.

SUMMARY OF THE INVENTION

The object of the invention is therefore to provide a construction which can be applied in a less critical way, and which still provides the required strength. This object is achieved in that an individually cast plate fits on the abutment element, which plate is to be connected to said element by an etching and/or an adhesive bonding technique, wherein the plate has a hole accommodating the pin.

In the construction according to the invention the forces exerted on the tooth prosthesis are safely carried by the pin, whereas the couples forces which try to rotate the tooth prosthesis around the pin counteracted by the cast plate.

A further, important improvement of the bearing capacity so the pin in the abutment element is achieved in case the pin has a local thickening which fits in the hole in the abutment element. The local thickening, which e.g. may be a separate delring of hemispherical shape fitted around the pin or may form a unity with the pin, fits in a predrilled widened part of the hole, whereby a greater bearing surface is obtained and local stresses are reduce.

According to a further embodiment, which improves the stability of the tooth prosthesis, the pin may carry an eccentrical stop means facing the abutment element for preventing rotation thereof, which stop means can be accommodated in a secondary hole in said element.

The construction thus obtained are finally treated by waxing so as to form them into a single piece.

The tooth prothesis may have a cavity which opens out in the tooth prothesis at its side facing away from its chewing or cutting face, for transversely sliding the tooth prothesis over the pin or the adaption pieces.

Onto said construction, the tooth prosthesis may be fixed permanently or removably.

In the latter case preferably, the cavity in the tooth prosthesis contains a cap which fits over the adaptation piece. Either the adaptation piece has an undercut hollow space and the cap has an inwardly protruding click piece which click fits into the hollow space, or the cap has an undercut hollow space, and the adaptation piece click fits into the hollow space.

This invention further concerns a construction for producing a fixed or a removable tooth replacement, consisting of at least one individually cast plate made of a suitable metal of choice, which is provided with an opening of defined size on the approximal side, at the level of the contact point; this plate is secured on the respective abutment element by means of an etching/adhesive bonding technique, and onto this there is then cast, welded or cemented an oval adaptation piece which has a concavely arched side surface and either a wedge-shaped or loop-shaped engagement incision on its top, and is equipped with a round opening at its center (which is congruent with the opening in the plate), and through which a movable pin which is milled from metal is fitted, which pin is held in the adaptation piece by a fastening screw and is additionally cemented in a small retention channel prepared for it in the abutment.

The invention relates to methods for producing a single-part or multi-part tooth replacement in the anterior tooth area or posterior tooth area between two abutment elements, which as far as possible are left intact when implementing said method.

This system solves the disadvantages and the indication restrictions which characterize the methods which are already known, such as the anchoring method described in the patent specifications 0025419, 0162808 and 0236264, and the conventional adhesive bridge.

The restrictions on the use of an adhesive bridge include, above all, the fact that no skeleton prosthesis, and only rather unpromising multi-part bridges, can be produced in the molar area. Its maximum loading capacity is in fact equal to the adhesive strength of the cement which used; apart from the retention afforded by the bonding, it has no other forms or mechanical retention by means of which its load-bearing capacity would be increased (see Nederlands Tandartsblad, volume 48, no. 9, page 421: Klinisch gedrag van posterior gevaardigde adhesiefbruggen [Clinical behaviour of posterior adhesive bridges], an article based on the dissertation: Posterior Resin-bonded Bridges, an in vitro and vivo study by C. W. G. J. Verzijden, Catholic University of Nijmegen, Mar. 3, 1993).

The plates or wings of an adhesive bridge often extend over a plurality of elements (which the patient may find uncomfortable) and have a defined size in order thereby to generate a sufficient retention surface. The occlusal supports which are sometimes necessary in such a construction interfere with the natural occlusion.

The novel development which is presented here remedies these disadvantages and at the same time reduces the damage to the abutments during preparation.

This is achieved by forming an individual plate (1) with an opening (2), which plate (1), in the case of sound abutment elements, is secured only on their approximal side by means of an etching/adhesive bonding technique. A specifically shaped adaptation piece (3) is then fitted on this plate, said adaptation piece (3) also having at its approximate center an opening (6) through which a movable pin (8) which is milled from metal is passed, is held in the adaptation piece by a fastening, screw (12) and is cemented in the abutment in a small channel (20) prepared for this purpose.

The mechanical pin retention, in conjunction with the chemical adhesion of the cement by the etching/adhesive bonding technique (in the case of pin and plate), guarantees a high load-bearing capacity, which is necessary for a multi-part tooth replacement in the molar area.

A number of indication restrictions of far-reaching consequence which are associated with the anchoring system already mentioned above are likewise remedied by this novel development. The anchors of the anchoring system can only be fitted in abutment elements which are fully stable and completely sound in the approximal area. It is this very area which is often affected by caries, and in such cases the anchoring system is not indicated.

The plate of this newly developed construction can be produced in any desired shape and covers any, restorations which may present. This is also of advantage, since composite restorations particular experience shrinkage over the course of time, and as a result a perfect border seal is not guaranteed in the long term (See: Nederlands Tandartsenblad, volume 48, no. 8, page 377, Directe restauraties in het posteriorgebied [Direct restoration in the posterior area].

The plate thus also serves as a protection for one element concerned.

It was found that the interdental space between anchor and bridge (anchoring system) is difficult to access for optimal cleaning, as a result of which secondary caries can develop over one course of time.

A further advantage of the novel development is the omission of preparations involving trimming the abutments for the attachment of the plates, which is of course necessary for both the methods mentioned above and is done at the expense of sound tooth substance.

The novel construction is fitted in the abutment element using only one pin, which makes the work easier and affords a number of advantages.

First, application is made easier for the dentist; no special instrumentation is required for preparing a small retention channel (this is done using standard devices).

Second, correct positioning of the construction on the abutments is made simpler. The successful accomplishment of this step of the operation is critical for a satisfactory aesthetic result. A pin can be fitted with greater precision at the contact point of the abutment element, which from the aesthetic point of view is like the trimming of a bridge.

Third, the indication range is extended. In the case of short clinical crowns, it is often not possible to use the dual-pin anchors. The anchor always has to lie flat on the abutment so as to prevent loosening as a result of friction; if, for reasons of lack of space, the flattening for the bearing of the anchor is set to deep, the cervical anchor pin could touch the pulp.

Fourth, the pin in the novel development has a greater diameter by comparison and is at the same time shorter, as a result of which, on the one hand, it can withstand a higher load and, on the other hand, the risk of pulp contact is generally diminished. For example, a 30% greater diameter can support 75% more load. The pin can therefore be shorter because it has a greater diameter, but the additional plate of the construction, which is secured by the etching/adhesive bonding technique, similarly takes up the compressive, shearing and tensile forces which occur. In addition, the pin is milled in a single piece from metal, and not cast, which fact also increases is load-bearing capacity.

In the anchoring method, a strengthening of the pins is not possible in this respect since the anchors thereby acquire a greater circumference. Moreover, the distance between the pins has to be at least 1.5 mm since the two retention channels in most cases have additional bore deflections, as a result of which their diameter is greater than the necessary 0.9 mm. Too little space between the pins would lead to fracturing of the tooth substance between the channels. In addition, the smallest of the dual-pin anchors is already 3.5 mm in height.

The pin in the novel construction has no retention grooves, and its strength is thus uniform over the entire surface area. In recent times it has become possible to dispense with retention grooves not only as a result of the improvement in cements, but also as a result of improvements in the methods used for preparing the respective adhesion surfaces, for example by silicatization.

Since the system is much more delicate as a result of the novel structural features, its range of possible uses is greater compared to the anchoring system, since the possibility of preparing the mutually facing retention channels in small diastemata is also dependent on the diameter of the drill head.

The oval adaptation piece has a concavely arched side surface (narrow side), as a result of which the bridge matrix acquires, over and above the cement binding, an additional mechanical retention.

The novel construction can also be used with mobile abutment elements, in which case these elements are stabilized simultaneously as if by splinting.

The combination of a plate, which is secured on the abutment by means of an etching/adhesive bonding technique, and of a pin, which is cemented in the abutment element, can withstand a multiple of the masticatory pressure occurring in the mouth.

BRIEF DESCRIPTION OF THE DRAWINGS

The construction is explained hereinbelow with reference to sketches.

With reference to FIG. 1, the construction may include individually cast plate 1 with the approximal opening 2 of defined size, through which the pin 8 is passed;
the oval adaptation piece 3 for a fixed tooth replacement;
wedge-shaped incision 4 on the top;
the concavely arched 5 outside;
the semispherically tapering opening 6 into which the pin 8 is introduced and in which the pin head bears;
thread 7 for the fastening screw 12;
the pin 8 milled from metal;
the cylindrical pin part 9 which is cemented in the element (prepared channel);
semispherical base 10 of the pin head;
concave surface 11 of the pin head;
semispherical base 13 of the fastening screw 12, fitting into the concave surface of the pin head 11;
thread 14;
hexagonal depression 15 in the fastening screw 12 as an attachment side for the screwing instrument 16;
screwing instrument 16.

FIG. 2 shows the variants of the adaptation piece 17.
Adaptation piece 17 for a removable tooth replacement;
loop-shaped engagement incision 18 on the top;
concave 5 outside;
semispherically tapering opening 6 in which the pin 8 is inserted (and in which the pin head and fastening screw bear);
thread 7 for the fastening screw 12;
adaptation piece 19 for a removable tooth replacement, which can be cast onto an artificial crown;
concave 5 outside;
loop-shaped engagement incision 18 on the top.

FIG. 3 shows an approximal view of a construction for a fixed tooth replacement, secured on an abutment element with screwing instrument.
Individually cast plate 1, secured on the element by an etching/adhesive bonding technique;
adaptation piece 3 which is cast on, welded on or cemented on;
fastening screw 12;
insertion site 15 for screwing instrument;
screwing instrument 16.

FIG. 4 shows an approximal view of a metal crown with cast-on adaptation piece for a removable tooth replacement.
adaptation piece 19 which can be cast on.

FIG. 5 shows the cross-section of an abutment element and of the patrix construction which is secured thereon.
individually cast plate 1, secured by means to an etching/adhesive bonding technique;
adaptation piece 3, 17 with tapering opening and thread, secured on the plate;
fastening screw 12;
pin 8, pivotable through approximately 15° in all directions;
prepared retention channel 20 with cement layer;
thread 14 of the fastening screw;
semispherical base 13 of the fastening screw;
semispherical base 11 of the pin head;
attachment site 15 for the screwing instrument.

FIG. 7 shows the modelling cap and approximal view of a patrix/matrix structure.
(21) modelling cap made of plastic for producing a matrix for a fixed tooth replacement;
(22) wedge-shaped protuberance fitting into the wedge-shaped incision (4) of the adaptation piece;
(23) convex inner surface fitting into the concave outside (5) of one adaptation piece;
(1) individually cast plate, secured on the abutment by means of an etching/adhesive bonding technique;
(24) metal matrix of the tooth replacement;
(3) adaptation piece for a fixed tooth replacement, secured on the plate;
(25) cement layer;
(12) fastening screw with depression for the screwing instrument.

FIG. 8 shows the transfer cap made of plastic, plastic lining of the patrix, and approximal view of a removable patrix/matrix construction.
(26) transfer cap made of plastic;
(27) bar-shared attachments for forming corresponding depressions in the metal matrix (holding arrangement for plastic lining);
(28) loop-shaped protuberance for fixing the position of the transfer cap in the adaptation piece in order to form the bridge matrix;
(23) convex inner surface;
(28) loop-shaped protuberance fitting into the corresponding incision on the top of the adaptation piece;
(27) bar-shaped attachments which fit into the recesses in the metal matrix;
(1) individually cast plate, secured by means of an etching/adhesive bonding technique;
(30) metal matrix of the tooth replacement;
(29) plastic lining, fixed by the bar-shaped attachments on the top of the metal matrix, clamped at the bottom in the loop-shaped incision of the adaptation piece: (17) adaptation piece with loop-shaped incision;
(12) fastening screw.

FIG. 10 shows a cross section through an element, in which the molding pin 33 has been applied in the channel. This molding pin 3 is removed from the element after molding, for manufacturing the final pin.

FIG. 11 shows parts of the patrix construction for fixed tooth prosthesis, wherein 1 is the individually cast plate on the approximal phase having an opening 2 for accommodating pin 8, 3 is the oval shaped adaptation piece for a fixed tooth prosthesis, and having a groove 4 at the top and a concavely shaped side 5, and opening 6 for accommodating the pin 8, the delring 34 with opening 35, and comprising a hemisperical shaped part 36 to be accommodated in the abutment element.

FIG. 12 shows the parts of the patrix construction for a removable tooth prosthesis, comprising a cup shaped adaptation piece 17, which has a concavely shaped side 5.

FIG. 14 shows an abutment element, in perspective and partly in cross-section having a patrix construction for a removable tooth prosthesis on the approximal face.

FIG. 15 shows the matrix cap 37 as a matrix for a fixed tooth prosthesis, bearing a ridge 38 fitting in the corresponding 4 of the oval shaped adaptation piece 3, and bearing outer ridges 39.

FIG. 16 shows a matrix cap 40 to be accommodated in the matrix of a removable tooth prosthesis, having a spherically shaped click element 41 fitting in a cap shaped adaptation piece, and having connecting ridges 26 fitting in grooves 26 of the matrix part of the removable tooth prosthesis.

Figure 1:
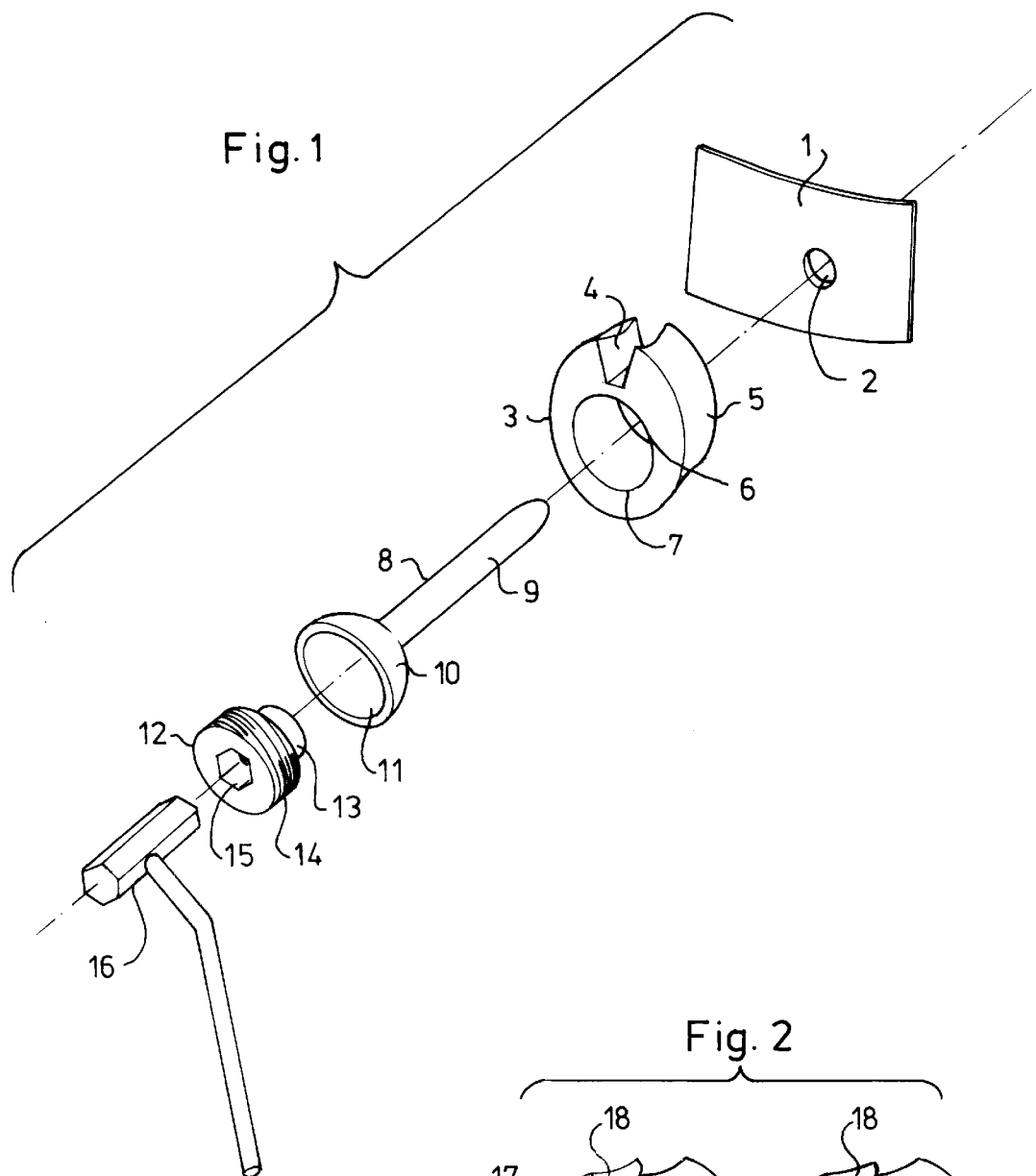
FIG. 1 shows the individual parts of a patrix construction for an abutment element.
Figure 2:
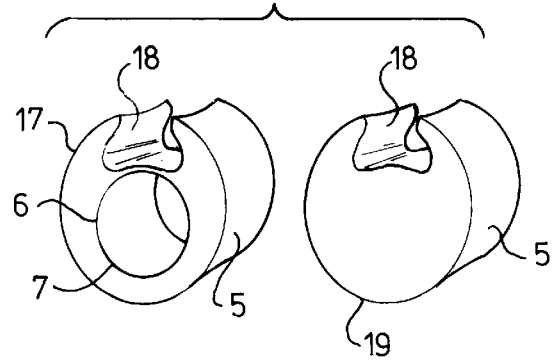
FIG. 2 shows the variants of the adaptation piece 17.
Figure 3:
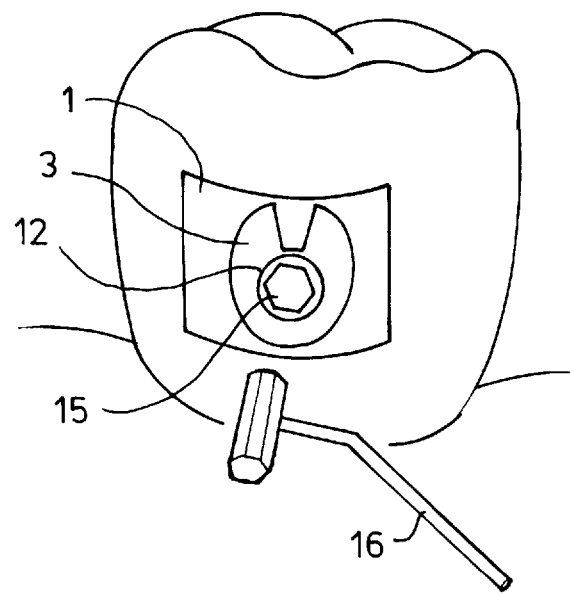
FIG. 3 shows an approximal view of a construction for a fixed tooth replacement, secured on an abutment element with screwing instrument.
Figure 4:
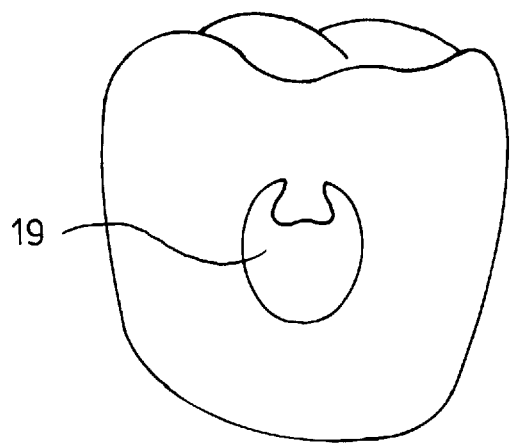
FIG. 4 shows an approximal view of a metal crown with cast-on adaptation piece for a removable tooth replacement.
Figure 5:
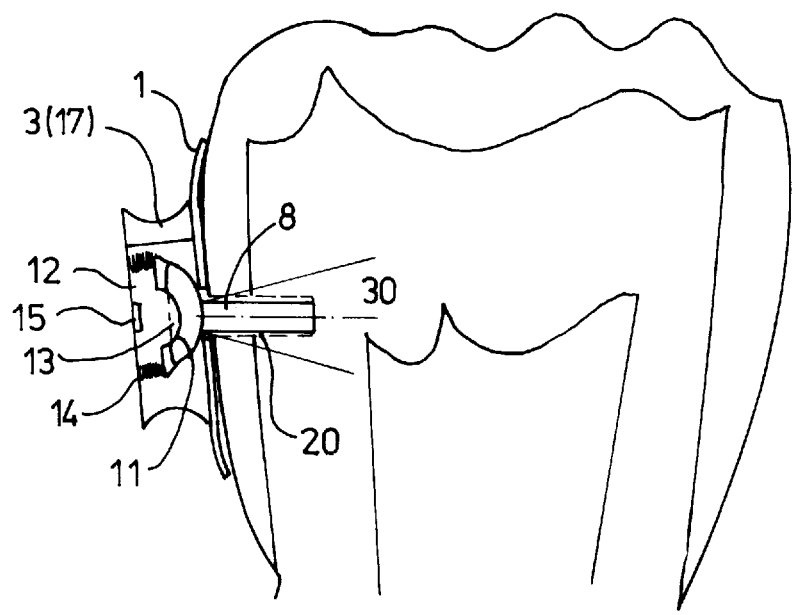
FIG. 5 shows the cross-section of an abutment element and of the patrix construction which is secured thereon.
Figure 6:
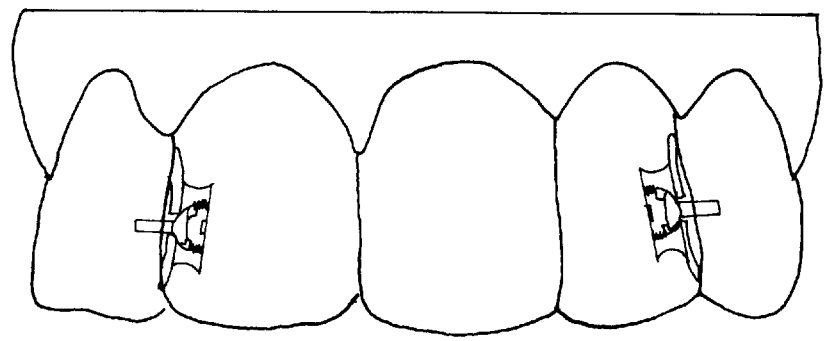
FIG. 6 shows a transparent front view of a three-part bridge, fitted on a patrix construction on the elements 12 and 23.
Figure 7:
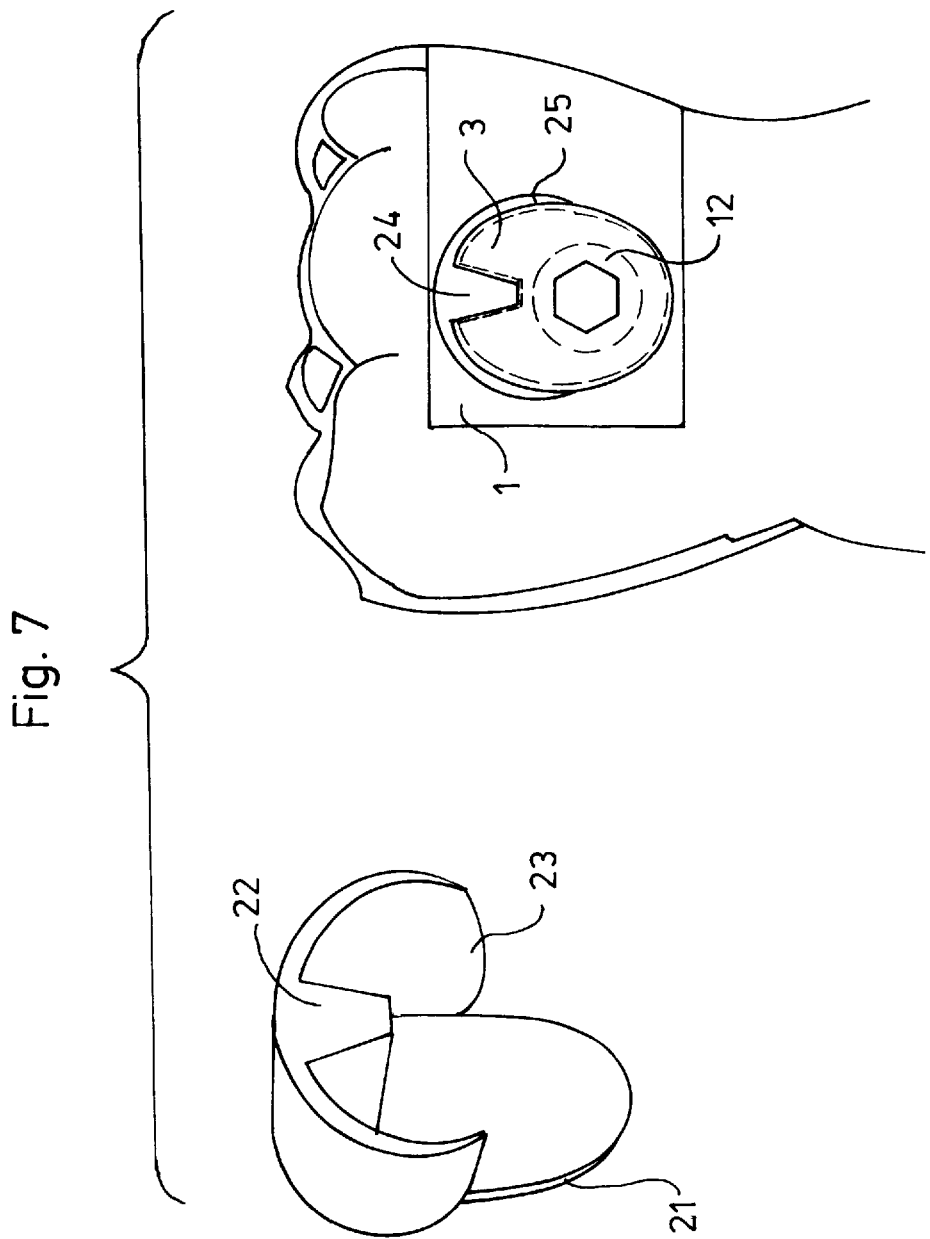
FIG. 7 shows the modelling cap and approximal view of a patrix/matrix structure.
Figure 8:
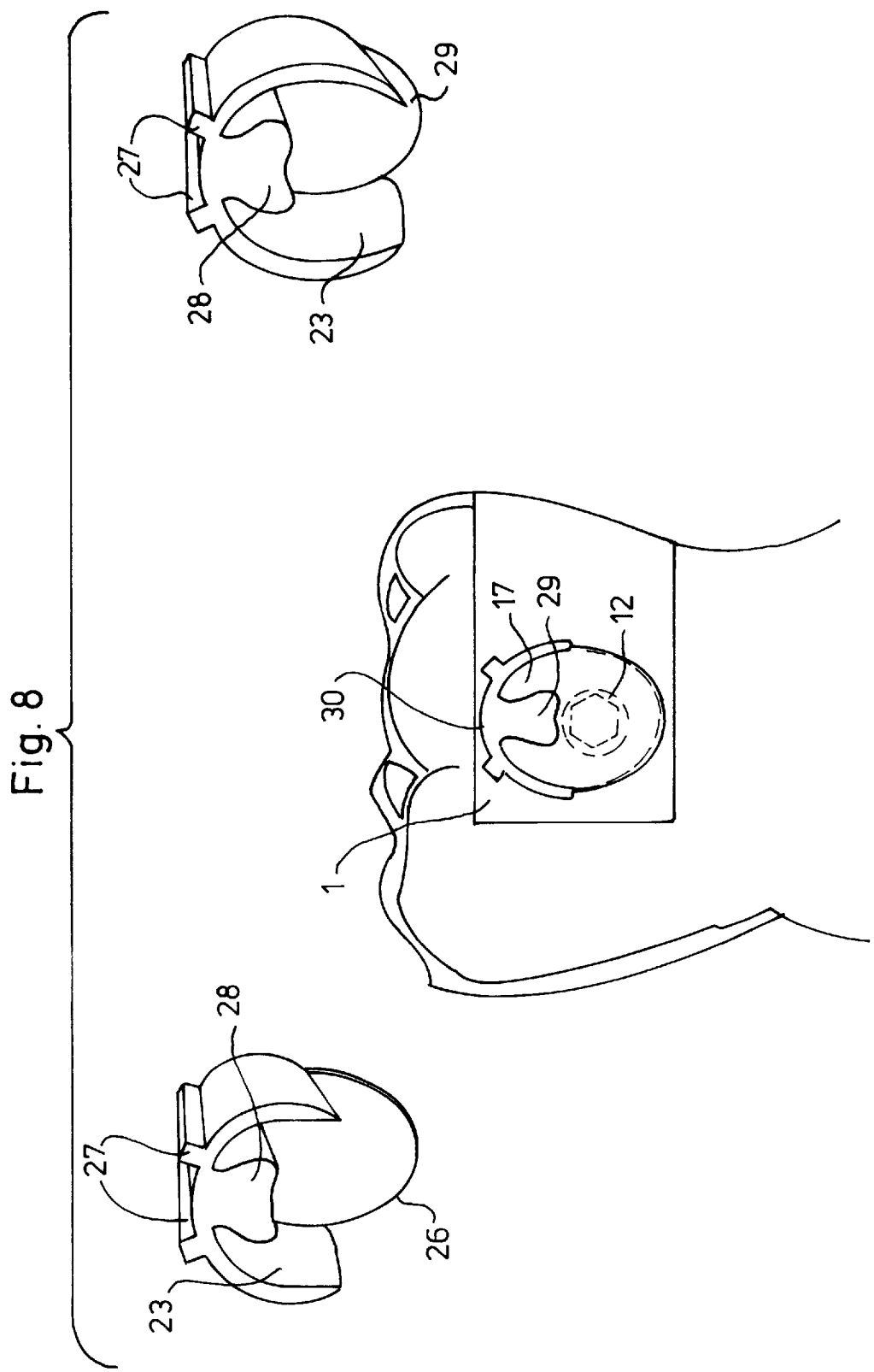
FIG. 8 shows the transfer cap made of plastic, plastic lining of the patrix, and approximal view of a removable patrix/matrix construction.

The working method for the embodiments of FIGS. 1–8 is described below.

Stage 1: Preparation by the dentist.

The dentist determines the point on the abutment element where the patrix construction is to be placed by marking the pin channel and determining the size and shape of the plate. An impression is taken of the clinical site.

Stage 2: Work in the dental laboratory.

The dental technician fits the adaptation piece (3 or 17) with the opening congruent with the drill channel in the abutment element of the plaster model. The plate is modelled with wax around this channel, following the instructions from the dentist, and is finally cast onto the adaptation piece.

The following procedure is also possible: First, the plate is modelled and cast, after which the adaptation piece is cemented or welded on.

The specific shape of the adaptation piece—an oval with a wedge-shaped (4) or loop-shaped (18) engagement incision at its top, which stabilizes the bridge matrix—also prevents rotation.

The adaptation piece with the wedge-shaped incision (4) is used for a fixed tooth replacement, while the one with the loop-shaped (18) incision is used for a removable system. The concavely arched outside (5) permits (in addition to the cement binding) a mechanical retention between adaptation piece with plate (patrix) and the attached bridge (matrix).

Stage 3: Plate/pin construction placed on the abutment elements by the dentist.

The dentist sets the pin channel marked on the respective abutment to the requisite depth and checks it using the pin (8). The plates with the corresponding adaptation piece are arranged on the two abutments by means of an etching/ adhesive bonding technique. The pin (8) which is milled from metal is passed through the opening in the patrix construction and into the prepared retention channel, and the pin part (9) is cemented in the element. The pin with its semispherical pin-head base (10) and concave top surface (11) is secured with a fastening screw (12). On the fastening screw there is a thread (14), and its semispherical base (13) fits into the concave top surface (11) of the pin head. The fastening screw is tightened using a screwing instrument (16) which fits into the depression (15) in the screw. At the end of this work stage, an impression is taken again, this time with the complete patrices in situ.

Stage 4: Production of a bridge in the dental laboratory.

If a removable tooth replacement is to be produced, the dental technician fits the transfer cap (26) onto the cast-on adaptation piece on the plaster model. This model is placed in duplicating composition, with the transfer caps in situ. The bridge matrix is finally modelled onto the duplicated model. The plastic lining (coating) (29) clamped into the cast metal matrix.

When a fixed tooth replacement is being made, the dental technician fits the modelling cans (21) onto the plaster model patrices and models the bridge part between them.

Stage 5: The dentist inserts the bridge.

In the case of a fixed tooth replacement, the bridge matrices are cemented onto the abutment patrices.

With this invention, both a fixed and also a removable, single-piece or multi-piece tooth replacement can be produced, the necessary preparations affecting a minimum amount of tooth substance; the application possibilities are numerous since restored abutment elements too, in the anterior tooth area and posterior tooth area, remain functional.

Figure 9:
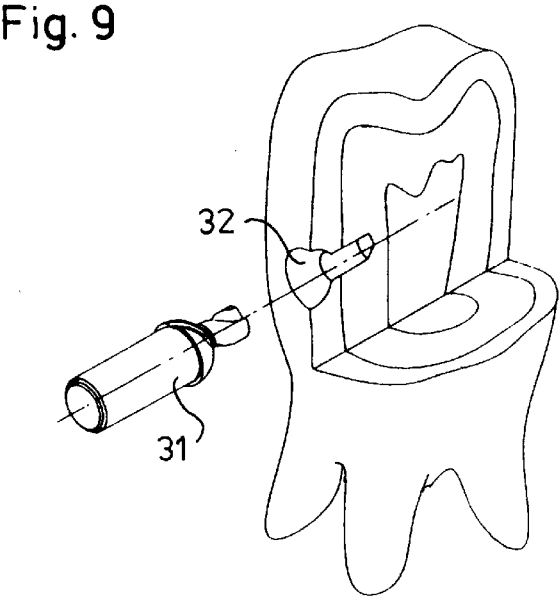
FIG. 9 shows an element in which a channel 32 has been prepared by a specially shaped drill 31.
Figure 10:
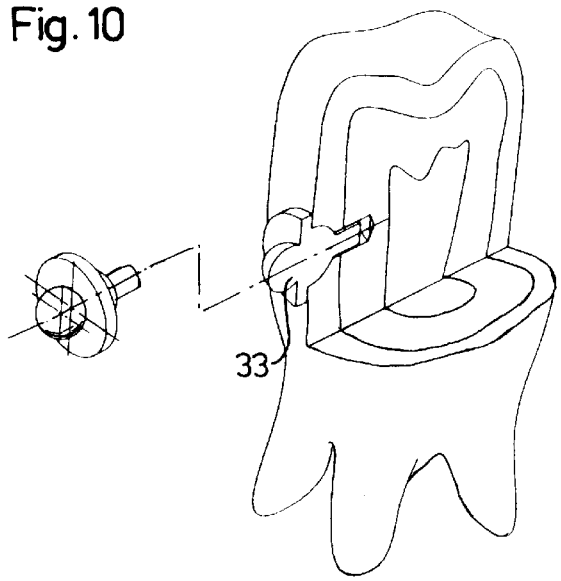
FIG. 10 shows a cross section through an element, in which the molding pin 33 has been applied in the channel.
Figure 11:
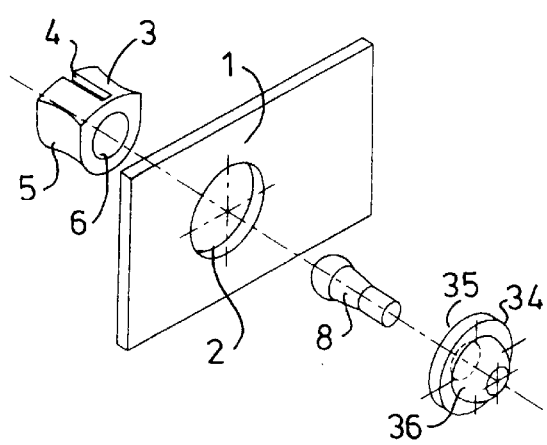
FIG. 11 shows parts of the patrix construction for a fixed tooth prosthesis.
Figure 12:
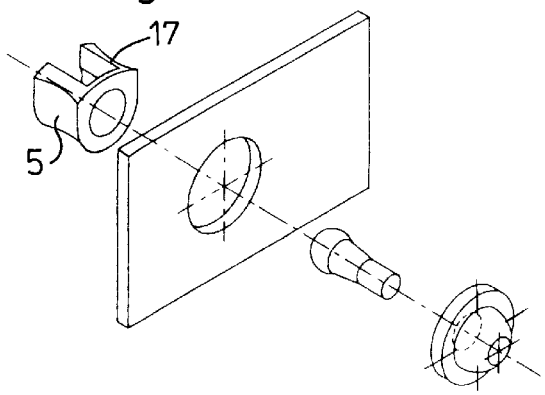
FIG. 12 shows the parts of the patrix construction for a removable tooth prosthesis.
Figure 13:
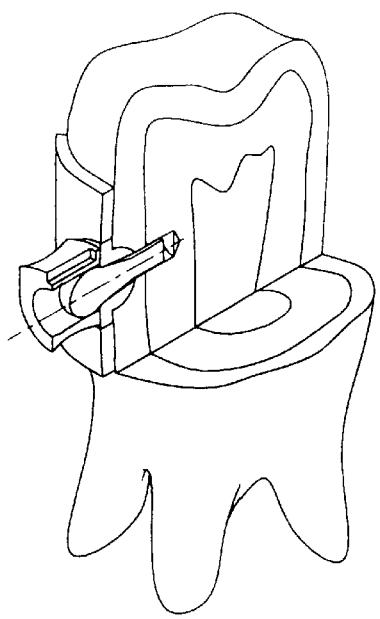
FIG. 13 shows an abutment element in perspective, partly in cross-section, bearing the patrix construction for a fixed tooth prosthesis on the approximal face.
Figure 14:
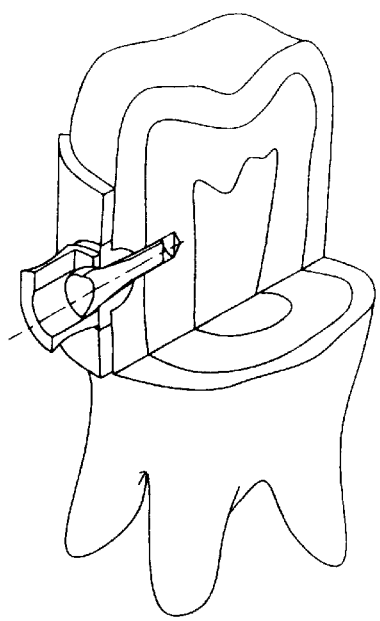
FIG. 14 shows an abutment element, and partly in cross-section having a patrix construction for a removable tooth prosthesis on the approximal face.
Figure 15:
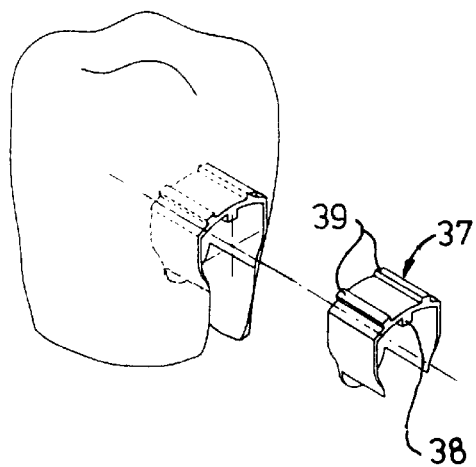
FIG. 15 shows the matrix cap as a matrix for a fixed tooth prosthesis.
Figure 16:
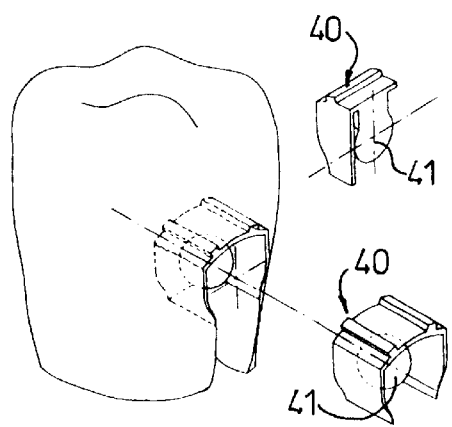
FIG. 16 shows a matrix cap to be accommodated in the matrix of a removable tooth prosthesis.
Figure 17:
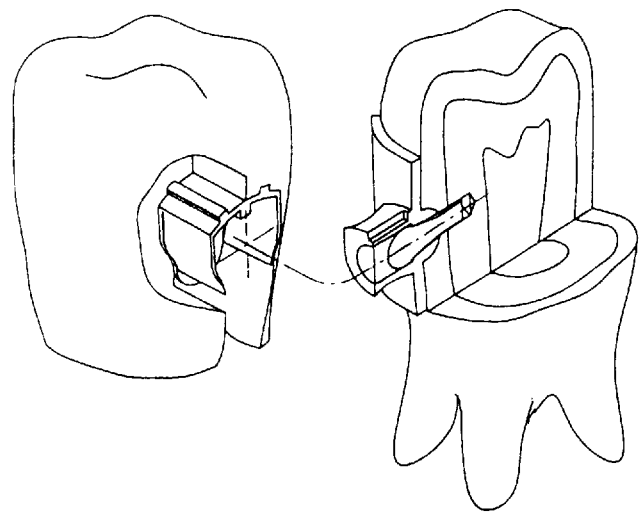
FIG. 17 shows the fitting of patrix and matrix for a fixed tooth prosthesis.
Figure 18:
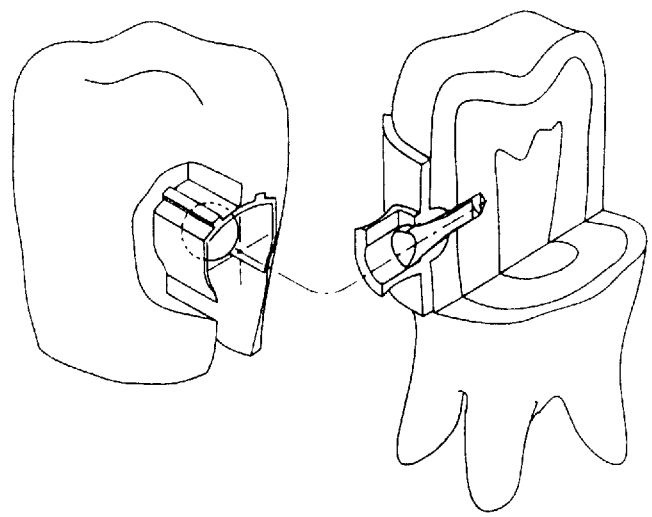
FIG. 18 shows the fitting of patrix and matrix in removable tooth prosthesis.

The working method for the embodiment of FIGS. 9–18 follows below.

Stage 1: pre-treatment by dentist.

The dentist determines the position for connecting the construction to the abutment elements, by means of marking the position for the pin 8 in the abutment element. Subsequently, he drills the channel 32 with a specially shaped drill 31; thereafter, the molding pin 33 is fitted in the channel. The molding pin is removed from the channel, whereafter a model is cast. In this cast model, the desired shape and dimensions of the individual plate 1 are determined, and the channel in the abutment element is provisionally filled.

Stage 2: in the dental laboratory.

The dental technician duplicates the model and places one delring 34 in the duplicating gel, whereafter the construction is cast in a mass. On this cast model, the individual plate 1 is shaped, which fits on the delring. Next, the adaptation piece 3 or 17 is placed onto the delring. Subsequently, the casting procedure is carried out.

The specific shape of the adaptation pieces, i.e. oval shaped with groove 4 serves for preventing rotation of the tooth prosthesis. The oval shaped adaptation piece 3 with groove is applied in the case of a fixed tooth prosthesis, whereas the cup shaped adaptation piece 17 is applied for a removable tooth prothesis. The concavely shaped outer sight 5 serves for providing a mechanical connection between the adaptation piece with plate (patrix) and the tooth prothesis (matrix).

Stage 3: The dentist removes the provisional filling from the channel and cements the cast parts by means of the etching/bonding method on the abutment element. The pin 8 protrudes through the plate in the adaptation piece, and is cemented into the channel.

After completion of this work, a mold is made.

Stage 4: Production of the tooth prosthesis by the tooth technician.

In the case of a removable tooth prosthesis, the dental technician places the matrix cap 40 onto the adaptation piece, which is present on the cast mold. Then, duplicating mass is cast over the model with matrix cap. Subsequently, onto the duplicate model thus obtained the matrix is modelled or shaped. The plastic matrix cap 26 is clamped in the cast matrix.

In the case of a fixed tooth prosthesis, the tooth technician places the matrix cup 37 on the cast model and subsequently models or shapes the bridge part to be cast.

Stage 5: The dentist places the tooth prosthesis.

In the case of a fixed tooth prosthesis, the matrix of the tooth prosthesis cemented onto the patrix construction.

The advantage of the invention is the provision of a fixed or removable tooth prosthesis which only gives a minimum damage of the tooth material, which offers a much larger indication area because of possible applications to unhealthy elements and in the molar area.

I claim:

1. A construction for a tooth prosthesis that is to be placed next to an abutment element with a recess therein, said construction comprising:
   a plate for conformable affixation to the abutment element, said plate having a hole there through for being placed in registration with the recess in the abutment element;
   an adaptation piece on said plate for holding the tooth prosthesis and comprising means for preventing rotation of the tooth prosthesis; and
   a pin inserted through said adaptation piece and through said hole in said plate and for being affixed in the recess in the abutment element.

2. Construction according to claim 1, wherein the pin has a local thickening for fitting into the recess in the abutment element.

3. Construction according to claim 2, wherein the thickening is a delring having a central hole accommodating the pin.

4. Construction according to claim 2, wherein the thickening is essentially hemisperical.

5. Construction according to claim 1, wherein the pin carries an eccentrical stop means for facing the abutment element for preventing rotation thereof, said stop means for being accommodated in a secondary hole in the abutment element.

6. Construction according to claim 5, wherein the stop means is an essentially hemispherical protrusion.

7. Construction according to claim 1, wherein the pin is connected to the adaptation piece.

8. Construction according to claim 7, wherein the pin has a head of enlarged diameter, and the adaptation piece has an internal space bounded by an end wall for facing the abutment element, which end wall has a hole the diameter of which is smaller than the corresponding diameter of the head of the pin, for hooking the adaptation piece onto the abutment element.

9. A construction for a tooth prosthesis that is to be placed next to an abutment element with a recess therein, said construction comprising:
   a plate for conformable affixation to the abutment element, said plate having a hole there through for being placed in registration with the recess in the abutment element;
   an adaptation piece affixed to said plate for carrying the tooth prosthesis, said adaptation piece comprising an incision in one side for preventing rotation of the tooth prosthesis and another side that is concavely arched;
   a pin inserted through said adaptation piece and through said hole in said plate and for being affixed in the recess in the abutment element; and
   a fastening screw for holding said pin in said adaptation piece.

10. Construction according to claim 9, wherein the incision (18) is loop-shaped.

11. Construction according to claim 9, wherein the incision (4) is wedge-shaped.

12. Construction according to claim 9, wherein the adaptation piece has a semispherically tapering opening (6) at its center.

13. Construction according to claim 12, further comprising a thread (7) in the adaptation piece, at the outer edge of the semispherical opening.

14. Construction according to claim 9, wherein the pin has a head with a concave surface (11) and a semispherical base (10).

15. Construction according to claim 9, wherein the fastening screw has a semispherical base (13).

16. Construction according to claim 9, wherein the fastening screw is provided with an attachment site (15) for a screwing instrument.

17. Construction according to claim 9, further comprising a modelling cap (21) that is a modelling aid for a fixed tooth replacement, said cap having a convexly arched inner side (23) and a wedge-shaped protuberance (22).

18. A construction for a tooth prosthesis that is to be placed next to an abutment element with a recess therein, said construction comprising:
   a plate for conformable affixation to the abutment element, said plate having a hole there through for being placed in registration with the recess in the abutment element;
   an adaptation piece on said plate for carrying the tooth prosthesis and comprising means for preventing rotation of the tooth prosthesis;
   an annular member for being affixed around the recess in the abutment element and having an outer diameter corresponding to a diameter of said hole; and
   a pin inserted through said adaptation piece, said hole in said plate, and through said annular member, and for being affixed in the recess in the abutment element.

* * * * *